United States Patent [19]

Carlson

[11] 4,097,743
[45] Jun. 27, 1978

[54] MOISTURE ANALYZING METHOD AND APPARATUS

[75] Inventor: Roger E. Carlson, Hopkinton, Mass.

[73] Assignee: Moisture Systems Corp., Hopkinton, Mass.

[21] Appl. No.: 788,750

[22] Filed: Apr. 19, 1977

[51] Int. Cl.² .............................................. G01J 1/00
[52] U.S. Cl. ................................... 250/339; 250/340
[58] Field of Search ............... 250/339, 340, 341, 343, 250/345; 340/248 A, 248 B, 248 C

[56] References Cited

U.S. PATENT DOCUMENTS

| 2,772,546 | 12/1956 | Barrows | 310/750 |
| 3,790,796 | 2/1974 | Brunton et al. | 250/339 |
| 3,820,099 | 6/1974 | Vogt | 340/248 B |
| 3,828,173 | 8/1974 | Knepler | 250/339 |

Primary Examiner—Alfred E. Smith
Assistant Examiner—Janice A. Howell
Attorney, Agent, or Firm—John E. Toupal

[57] ABSTRACT

A moisture analyzer including a first optical system for receiving radiant energy from a source and producing therewith first and second radiant energy beams having a given band of wavelength readily absorbable by moisture and a second optical system for receiving energy from the source and producing therewith third and fourth radiant energy beams having a common band of wavelength less readily absorbable by moisture. An optical director system directs the first and third beams to a sample being analyzed and then to a photodetector and directs the second and fourth beams directly to the photodetector without contacting the sample. In response to the output of the photodetector, an output circuit produces an electrical signal dependent upon a relationship $$\frac{V_r}{V_m} \times \frac{V_{m'}}{V_{r'}}$$

where $V_m$ is a signal value dependent upon the detected energy level of the first beam, $V_{m'}$ is a signal value dependent upon the detected energy level of the second beam, $V_r$ is a signal value dependent upon the detected energy level of the third beam and $V_{r'}$ is a signal value dependent upon the detected energy level of the fourth beam. The term $Vr/Vm$ is a ratio of the different levels of energy absorbed by moisture from the first and third beams of different wavelength and therefore is a measurement of the moisture content in the sample. Conversely, the second and fourth beams that produce the signal $V_{m'}$ and $V_{r'}$ are not affected by moisture content of the sample. They are influenced, however, by any temperature induced optical transmission changes in exactly the same manner as are the first and third beams that produce the signals $V_r$ and $V_m$. Thus, any inaccuracies that would result from such transmission changes are canceled from the moisture indicating output signal $$\frac{V_r}{V_m} \times \frac{V_{m'}}{V_{r'}}.$$

40 Claims, 16 Drawing Figures

MOISTURE ANALYZING METHOD AND APPARATUS

BACKGROUND OF THE INVENTION

This invention relates generally to a method and apparatus for material analysis and, more particularly, to a method and apparatus employing infrared radiation to measure the moisture content of materials.

Present conventional infrared moisture analyzers are two beam instruments utilizing energy from two center wavelength beams to develop a signal proportional to percent moisture in a sample. One narrow band of wavelength is centered upon a region of the spectrum that is absorbed by the water contained within materials. Another narrow band of wavelength is centered upon a region which does not exhibit this absorption phenomenon. The two individual narrow band energy regions are commonly termed "measure" and "reference", respectively. The amount of energy reflected from the sample at each band, measure and reference, is commonly used in the following equation to determine material moisture content:

$$\% \text{ Moisture} = \frac{\text{Reference Energy (Reflected)}}{\text{Measure Energy (Reflected)}}$$

Where Reference Energy (Reflected) and Measure Energy (Reflected) are measured as the difference between no energy reflected (Dark Resistance) and the reflected energy measured in quantities such as peak voltage amplitude, resistance change, received power level or other parameters that can be measured on a photosensitive detector.

Conventional infrared moisture analyzers employ a broad band energy source; commonly a tungsten filament lamp, a rotating wheel containing narrow band optical filters and a photosensitive detector. Other components used include lenses and mirrors for proper focusing and directing of the beams. The temperature sensitivity of these components adversely affects the stability and accuracy of the instruments. The principal causes of instability and variation are center wavelength changes, bandwidth changes and transmission changes in the optical filters with varying ambient temperature. The lamp sources and detectors also contribute to a lesser degree to undesirable drift with temperature.

SUMMARY OF THE INVENTION

The invention is a moisture analyzer including a first optical system for receiving radiant energy from a source and producing therewith first and second radiant energy beams having a given band of wavelength readily absorbable by moisture and a second optical system for receiving energy from the source and producing therewith third and fourth radiant energy beams having a common band of wavelength less readily absorbable by moisture. An optical director system directs the first and third beams to a sample being analyzed and then to a photodetector and directs the second and fourth beams directly to the photodetector without contacting the sample. In response to the output of the photodetector, an output circuit produces an electrical signal dependent upon a relationship $$\frac{V_r}{V_m} \times \frac{V_{m'}}{V_{r'}}$$

where $V_m$ is a signal value dependent upon the detected energy level of the first beam, $V_{m'}$ is a signal value dependent upon the detected energy level of the second beam, $V_r$ is a signal value dependent upon the detected energy level of the third beam and $V_{r'}$ is a signal value dependent upon the detected energy level of the fourth beam. The term $V_r/V_m$ is a ratio of the different levels of energy absorbed by moisture from the first and third beams of different wavelength and therefore is a measurement of the moisture content in the sample. Conversely, the second and fourth beams that produce the signals $V_{m'}$ and $V_{r'}$ are not affected by moisture content of the sample. They are influenced, however, by any temperature induced optical transmission changes in exactly the same manner as are the first and third beams that produce the signals $V_r$ and $V_m$. Thus, any inaccuracies that would result from such transmission changes are canceled from the moisture indicating output signal $$\frac{V_r}{V_m} \times \frac{V_{m'}}{V_{r'}}.$$

In a preferred embodiment of the invention, the optical systems include collimators for producing a measure and a compensating radiant energy beam and a rotary wheel supporting both a first optical filter for transmitting the moisture absorbable wavelength and a second optical filter for transmitting the less moisture absorbable wavelength. During rotation of the wheel, the first and second filters periodically move into axial alignment with the measure and compensating beams so as to produce in a timed sequence the first and third beams that are directed to the sample and reflected thereby to the photodetector and the second and fourth beams that are transmitted directly thereto. This arrangement results in identical optical properties for the first and second beams and for the third and fourth beams thereby insuring an accurate cancellation from the output signal of errors incident to temperature induced optical transmission changes. In addition, the time sequencing of the beams permits detection of their energy levels with a single photodetector.

According to special features of the invention, the optical systems include an energy accumulator for providing the measure beam with a higher energy level than the compensating beam and an adjustable attenuator for adjusting the energy levels of the second and fourth beams produced from the compensating beam. Because none of its energy is absorbed by the sample, the compensating beam requires less initial energy content while the attenuator permits adjustment of the compensating beam's energy transmission characteristics.

Another feature of the invention is a commutator system associated with the rotary wheel and effective to generate timing pulses that indicate periods in which the first and second optical filters are axially aligned with the measure and compensating beams and distinguishable periodic pulses that identify the sequence of the timing pulses. The timing and periodic pulses are employed in a decoder section of an electronic processor to separate from an ac output signal of the photodetector those portions representing the specific energy levels in each of the first, second, third and fourth beams. In a preferred embodiment, the commutator system includes a plurality of reflective mirrors strategically located on the surface of the rotary wheel and accommodated by a stationary sensor comprising a light source for directing light onto the mirrors and a light detector for receiving reflected light therefrom.

Another feature of the invention is an electronic processing system including log converters that derive log signals proportional to log values of the photodetector output signals $V_r$, $V_{r'}$, $V_m$ and $V_{m'}$; a summing circuit that produces a composite log signal with a value proportional to the sum of the log signals derived from the signals $V_r$ and $V_{m'}$ less the sum of the log signals derived from the signals $V_{r'}$ and $V_{m'}$; and an antilog converter that produces an analog output signal with a value proportional to the antilog value of the composite log signal. The processor circuit provides in a simple and efficient manner a moisture indicating output signal dependent upon the desired relationship $$\frac{V_r}{V_m} \times \frac{V_{m'}}{V_{r'}}.$$

In a preferred embodiment the processing circuit employs transistors as log and antilog converters and utilizes the inherent logarithmic relationship between their collector current and base-emitter voltage.

Still another feature of the invention is the use of a balanced differential input circuit as a preamplifier for the output of the photodetector. The high common mode rejection preamplifier circuit cancels from the photodetector output all noise and ripple currents introduced through interconnecting wiring, power supply noise and ripple or resulting from instability caused by component temperature drift. Because of this noise rejection, the analyzer is rendered sensitive to extremely small changes in detected light level.

A further feature of the invention is a fault detector that monitors voltage level or pulse train presence in each of a plurality of integrated circuit boards utilized in the analyzer's electrical systems. In the event of an abnormality in the monitored voltages or pulse trains in any specific circuit board, a signal light associated with that board is energized. With the location of the fault thus identified, repair of the abnormality is greatly simplified.

Yet another feature is a lost motion coupling between the optical filter supporting rotary wheel and a drive motor therefor. The coupling comprises a flexible shaft that permits a given degree of relative axial movement between a motor shaft coupled to the motor and a wheel shaft coupled to the rotary wheel. Because of the flexible coupling a reduced starting torque is required permitting the use of a smaller drive motor. This in turn reduces heat dissipation which is important when the analyzer is being utilized in a high temperature environment.

Another feature of the invention is present in a housing for the photodetector and the optical director system. The housing comprises a flat window for transmitting the measure beams to the sample and the reflections therefrom to the photodetector and an optical shield for shielding the photodetector from radiant energy reflected by the window incident to the transmission of the beams to the sample. By eliminating reflections from the flat transmission window the ambient light level on the photodetector is reduced and its sensitivity improved. Furthermore this desirable result is obtained without the use of a relatively expensive domed window often used to eliminate reflection.

Another feature of the invention is the provision of an active dc restoration system that periodically grounds the output of the photodetector so as to establish a known base dc level desirable for accurate signal amplitude measurement. The dc restoration system prevents changes in dc output base levels that would result from varying levels in ambient light reflected from the sample onto the photodetector.

DESCRIPTION OF THE DRAWINGS

These and other objects and features of the invention will become more apparent upon a perusal of the following description taken in conjunction with the accompanying drawings wherein.

DESCRIPTION OF THE PREFERRED EMBODIMENT

Figure 1:
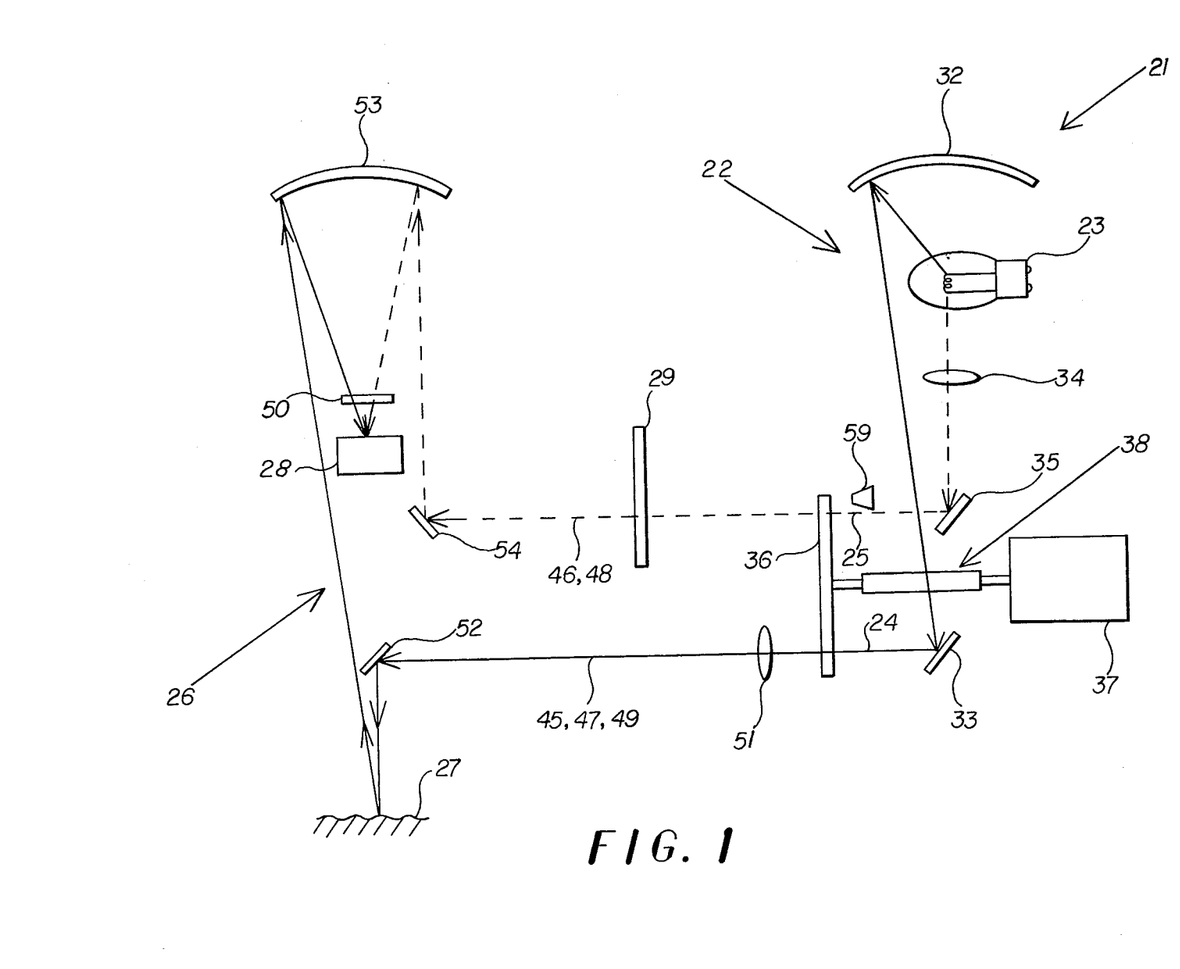
FIG. 1 is a schematic layout of an optical system for the invention.

Schematically illustrated in FIG. 1 is an apparatus 21 especially suited for determining the moisture content of various materials. An optical system 22 receives radiant energy from a light source 23 and produces therewith a measure light beam 24 and a compensating light beam 25. An optical director system 26 first directs the measure beam 24 to a sample 27 being analyzed and then directs radiant energy reflected by the sample 27 to a photodetector 28. Also directed to the photodetector 28 by the director system 26 is the compensating beam 25 after attenuation thereof by an aperture adjustment 29.

Figure 2:
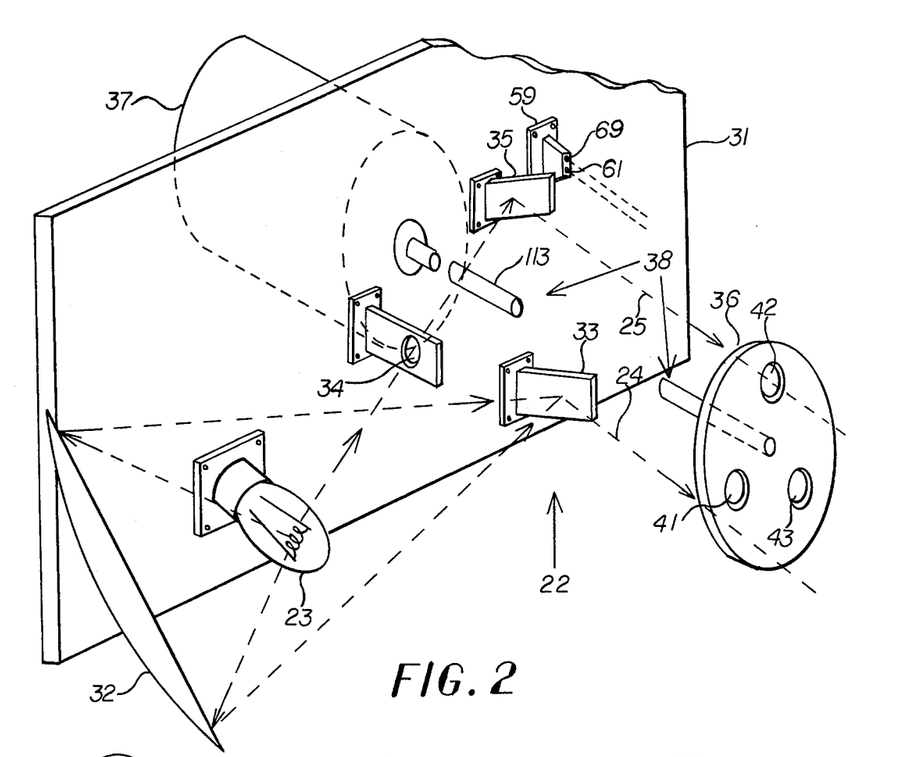
FIG. 2 is a partially exploded schematic, perspective view of a portion of the optical system shown in FIG. 1.

FIG. 2 schematically illustrates in a perspective and partially exploded view the optical system 22 which is integrally mounted on a support plate 31. Light from the source 23 is accumulated and collimated by a domed collecting mirror 32 and reflected by a mirror 33 as the measure beam 24. Light from the source 23 is collimated also by a condensing lens 34 and reflected by a mirror 35 as the compensating beam 25 that is parallel to the measure beam 24. The beams 24 and 25 are directed onto diametrically opposed locations on a rotary wheel 36 that is coupled to a drive motor 37 by a shaft assembly 38 described in greater detail below. Mounted on the wheel 36 is a first optical filter 41 that passes light only in a narrow infrared wavelength band readily absorbed by moisture, for example a band of 500 A° centered at 1.9 microns, a second optical filter 42 that passes light only in a narrow infrared wavelength band less readily absorbed by moisture, for example a band of 500 A° centered at 1.8 microns and a visible light window 43.

Figure 3A:
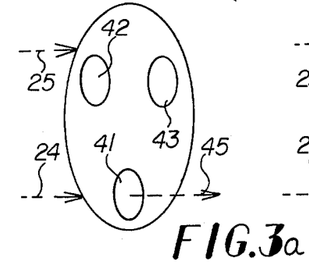
FIGS. 3a–3e are diagrammatic views illustrating operation of the optical system shown in FIG. 2.
Figure 3B:
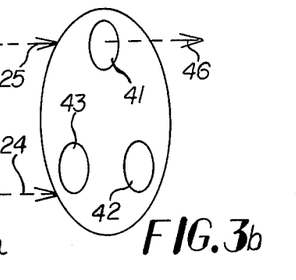
Figure 3C:
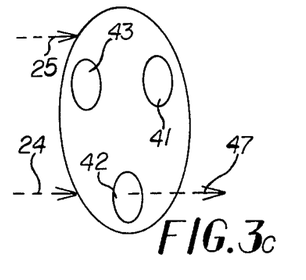
Figure 3D:
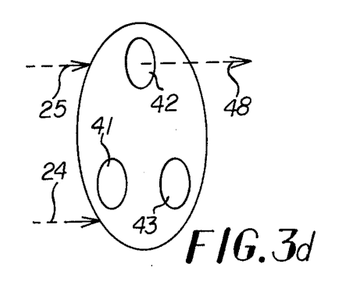
Figure 3E:
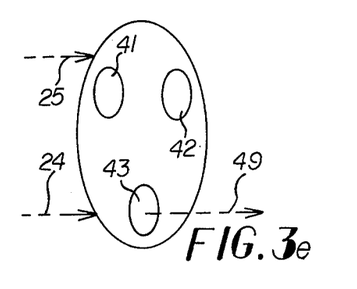

The filters 41 and 42 and the window 43 are equally spaced 120° apart and positioned so as to sequentially move through the beams 24 and 25 during rotation of the wheel 36. Also, the alignment of the optical system 22 is such that the measure and compensating beams 24, 25 pass through identical portions, respectively, of the first optical filter 41 and the second optical filter 42. Thus, as the wheel 36 rotates, the filters 41 and 42 become axially aligned alternately with the measure and compensating beams 24 and 25 producing therefrom a plurality of periodic beams as diagramatically illustrated in FIG. 3. In the wheel position of FIG. 3a, the filter 41 is axially aligned with and transmits the measure beam 24 producing a first beam 45 while the compensating beam 25 is obstructed by a solid portion of the wheel 36. After 180° of clockwise rotation by the wheel 36 (FIG. 3b) the filter 41 coincides with the compensating beam 25 so as to produce therefrom a second beam 46 having the same narrow band of wavelength as the first beam 45. In a position of the wheel 36 (FIG. 3c) displaced clockwise by 60° from the position shown in FIG. 3b, the second optical filter 42 coincides with the measure beam 24 producing a third beam 47 having a different band of wavelength than the first beam 45 but axially aligned therewith. FIG. 3d illustrates a fourth position of the wheel 36 wherein the second optical filter 42 coincides with the compensating beam 25 producing therefrom a fourth beam 48 having the same wavelength band as the third beam 47 but axially aligned with the second beam 46. Thus, the rotating wheel mounted filters 41 and 42 sequentially produce time sequenced first and second beams 45 and 46 having one moisture absorbent band of wavelength and third and fourth beams 47 and 48 having a different non-moisture absorbent band of wavelength. Finally in FIG. 3e there is illustrated a wheel position wherein the window 43 coincides with the measure beam 24 producing a visible light beam 49 that is axially aligned with the first and third beams 45 and 47. The function of the periodic visible beam 49 is merely to illuminate the sample location on which the infrared beams 45 and 47 impinge thereby simplifying alignment of the equipment. It will be appreciated that in still another position of the wheel 36, the window 43 also will become aligned with the compensating beam 25. However, that occurrence is merely coincidental and serves no particular function in the operation of the system.

Figure 4:
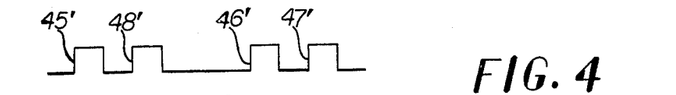
FIG. 4 is a waveform of a signal generated by the system shown in FIG. 1.

The director system 26 (FIG. 1) includes a lens 51 and a mirror 52 that direct the first and third infrared beams 45 and 47 and the visible beam 49 onto the sample 27. Resultant radiant energy reflected from the sample 27 is collected by a domed mirror 53 and reflected through a visible light blocking filter 50 onto the photodetector 28. Conversely, the second and fourth infrared beams 46 and 48 produced by the optical system 22 are reflected by a mirror 54 and the mirror 53 directly to the photodetector 28 without impinging on the sample 27. Thus in timed sequence, the photodetector 28 receives distinct bursts of radiant energy present in the periodic, non-concurrent beams 45-48. In response to these energy bursts, the photodetector 28 produces an ac output (FIG. 4) comprising distinct pulses representing the levels of the radiant energy bursts reaching the photodetector 28. As indicated in FIG. 4, the photodetector 28 sequentially produces a pulse 45' representing that energy portion of the first infrared beam 45 reflected by the sample 27 to the photodetector 28, a pulse 48' representing the energy level of the fourth infrared beam 48 received by the photodetector 28, a pulse 46' representing the energy level of the second infrared beam 46 received by the photodetector 28 and a pulse 47' representing that energy portion of the third infrared beam 47 reflected by the sample 27 to the photodetector 28. It will be appreciated that this pulse sequence will be repeated as the rotating wheel 36 continuously and sequentially moves the filters 41 and 42 through the measure and compensating beams 24 and 25 to produce the periodic beams 45-48. The visible beam 49 is eliminated by the filter 50 and therefore produces no output by the photodetector 28. As noted above, the function of the visible beam 49 is merely to illuminate the sample 27 and thereby indicate the optical alignment of the system.

Figure 5:
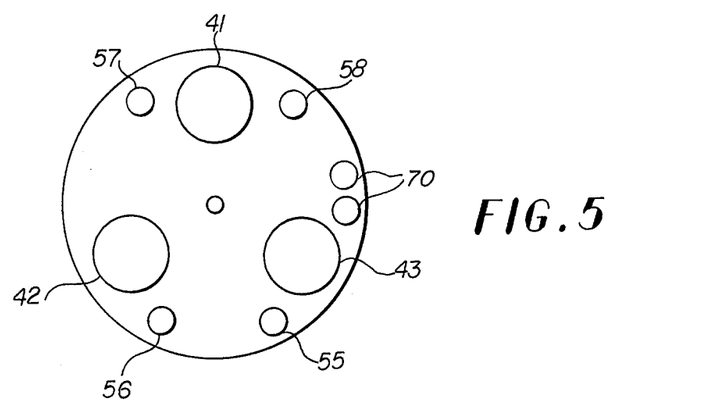
FIG. 5 is a schematic front plan view of a rotary wheel shown in FIGS. 1 and 2.
Figure 6:
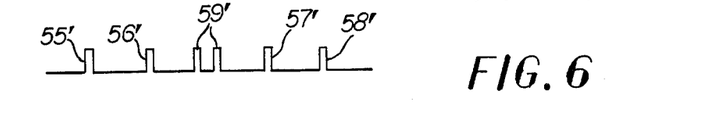
FIG. 6 is a waveform generated by a commutator system shown in FIGS. 2 and 5.

Rotary motion of the wheel 36 also generates commutator pulses for use in processing the photodetector output illustrated in FIG. 4. Distributed around the periphery of the front face of the wheel 36 are a plurality of commutator mirrors 55-58, as shown in FIG. 5. The mirrors 55-58 cooperate with a commutator sensor 59 (FIG. 2) to generate the commutator pulses. At each of a number of predetermined precise angular positions of the wheel 36, one of the commutator mirrors 55-58 receives light from a light emitting diode 61 mounted in the commutator sensor 59. The received light is reflected by the commutator mirror back to the sensor 59 where it is detected by a phototransistor 62 that produces a timing pulse indicative of that position. Thus, the sensor 59 produces a pulse train with a waveform as shown in FIG. 6 which is vertically related in time with the waveform of FIG. 4. The relative positions of the components are such that the mirror 55 induces a timing pulse 55' simultaneously with the pulse 45' caused by coincidence between the first filter 41 and the measure beam 24; the mirror 56 induces a timing pulse 56' simultaneously with the output pulse 48' caused by coincidence between the second optical filter 42 and the compensating beam 25; the commutator mirror 57 induces a timing pulse 57' simultaneously with the output pulse 46' caused by coincidence between the first optical filter 41 and the compensating beam 25; and the commutating mirror 58 induces a timing pulse 58' simultaneously with the output pulse 47' caused by coincidence between the second optical filter 42 and the measure beam 24. Also mounted along the periphery of the wheel 36 between the commutator mirrors 55 and 58 are an additional pair of initiator mirrors 70. These mirrors also reflect light from the light emitting diode 61 to the phototransistor 69. In response to the periodic movement of the initiator mirrors 70 by the commutator sensor 59 the phototransistor 62 generates periodic pulse pairs 59' as shown in FIG. 6. Since the spacing between the initiator mirrors 70 is less than the spacing between any of the other possible pairs of mirrors on the wheel 36, the periodic pairs 59' can be distinguished from the commutator timing pulses 55'-58'.

Figure 7:
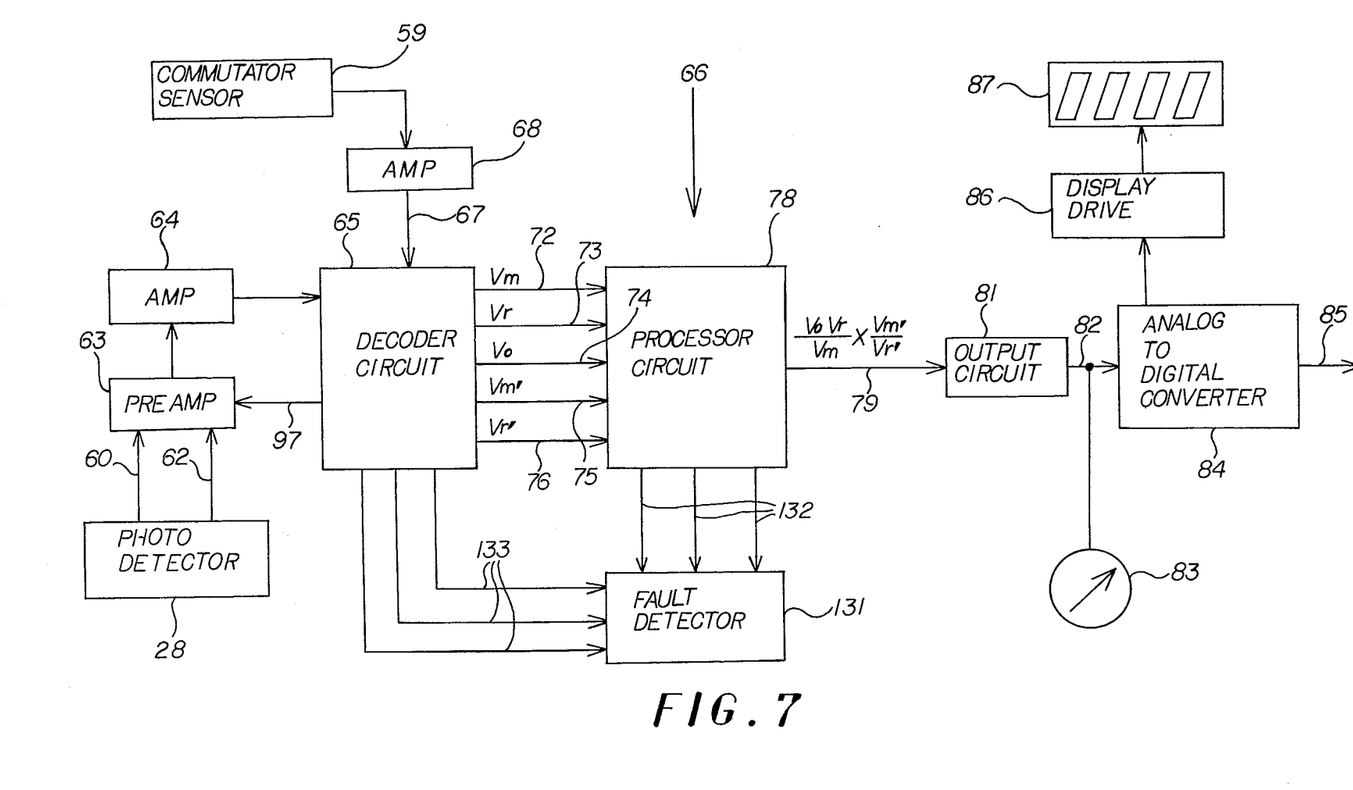
FIG. 7 is a schematic block diagram of an electrical system for use with the optical system of FIG. 1.

Referring now to FIG. 7 there is shown in block diagram form an electrical system 66 for use with the optical system 21 shown in FIGS. 1 and 2. The ac output (FIG. 4) of the photodetector 28 is fed on lines 60 and 62 to a preamplifier 63 described in greater detail below. Receiving the output of the preamplifier 63 is an amplifier 64 that supplies a signal to a signal decoder circuit 65.

The decoder circuit 65 also receives on a line 67 the commutator timing pulses 55′–58′ and the periodic pulses 59′ (FIG. 6) from the commutator sensor 59 after amplification in an amplifier 68. In response to the commutator timing pulses on line 67, the decoder circuit 65 separates the photodetector output into a plurality of dc voltage outputs on lines 72–76. These outputs include on a line 72 a voltage $V_m$ derived from the pulses 45′ (FIG. 4) and dependent upon the detected, sample reflected energy level of the first beam 45 (FIG. 1); on a line 73 a voltage $V_r$ derived from the pulses 47′ and dependent upon the detected, sample reflected energy level of the third beam 47; on a line 75 a voltage $V_{m'}$ derived from the pulses 46′ and dependent upon the energy level of the second beam 46; and on a line 76 a voltage $V_{r'}$ derived from the pulses 48′ and dependent upon the detected energy level of the fourth beam 57. Another output of the decoder circuit 65 on a line 74 is a reference voltage $V_o$. The decoder circuit also feeds to the preamplifier 63 on a line 97 a switch control signal that is synchronized with the periodic pulses 59′ (FIG. 6) from the sensor 59.

Receiving the signal voltages on lines 72–76 is a signal processor circuit 78 that is described in greater detail below. The output of the processor circuit 78 on a line 79 is an output voltage $$\frac{V_o V_r}{V_m} \times \frac{V_{m'}}{V_{r'}}.$$

The term $V_o V_r / V_m$ represents a ratio of the different levels of energy absorbed by sample moisture from the first and third beams of different wavelength and therefore is a measurement of the moisture content in the sample. Conversely, the second and fourth beams that produce the values $V_{m'}$ and $V_{r'}$ are not affected by moisture content of the sample. They are influenced, however, by any temperature induced optical transmission changes in exactly the same manner as are the first and third beams that produce the signal values $V_r$ and $V_m$. Thus, any inaccuracies that would result from such transmission changes are canceled from the output signal $$\frac{V_o V_r}{V_m} \times \frac{V_{m'}}{V_{r'}}$$

which is an accurate indicator of sample moisture content. Receiving the signal on line 79 is an output circuit 81 having on a line 82 an analog signal indicative of sample moisture content and displayed by a meter 83. Also receiving the analog signal on line 82 is an analog-to-digital converter circuit 84 that produces on line 85 a digital output indicative of sample moisture content. The analog-to-digital converter circuit 84 also provides an input to a display driver 86 that controls a digital display 87.

Figure 8:
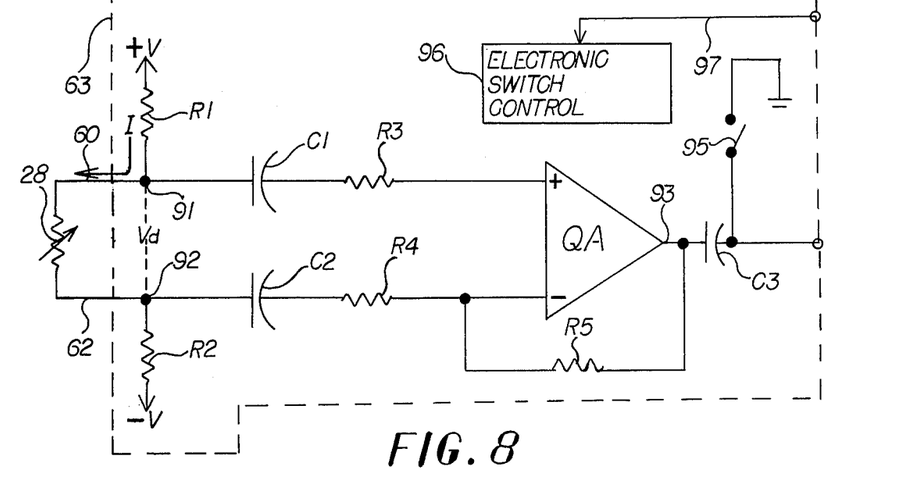
FIG. 8 is a schematic circuit diagram of a preamplifier shown in FIG. 7.

FIG. 8 illustrates circuit details of the preamplifier circuit 63 shown in FIG. 7. One input on line 60 from the photodetector 28 is received at an input terminal 91 connected to a positive voltage source by a load resistor R1 while the other photodetector input on line 62 is applied to a terminal 92 that is connected to a negative voltage source by a load resistor R2. Also connected to the input terminal 91 by a coupling capacitor C1 and an input resistor R3 is the positive input of an operational amplifier QA. Similarly, the input terminal 92 is connected to the negative input of the amplifier QA by a coupling capacitor C2 and an input resistor R4. Connecting the output 93 of the amplifier QA to the negative input is a feedback resistor R5. The signal output (FIG. 4) of the amplifier QA is applied through a coupling capacitor C3 to the amplifier 64 shown in FIG. 7. Connected between ground and the coupling capacitor C3 is a switch 95 that is actuated by an electronic control circuit 96 in response to pulses received from the decoder circuit 65 (FIG. 7) on a line 97.

The resistance of the photodetector 28, preferably a lead sulphide detector, is directly proportional to the amount of light impinging upon it. To enhance the analyzer system's sensitivity to extremely small changes in light level, the present invention provides for the output of the photodetector 28 a highly noise-immune preamplifier 63. The balanced differential input circuit shown in FIG. 8 establishes the desirable noise immunity. A current (I) flows from the positive supply (+V) to the negative supply (−V) through the detector 28. The resistances R1 and R2 are fixed value load resistors while variations in impinging light levels induce changes in the resistance of the sensing detector 28. These resistance changes in turn cause changes in the voltage $V_d$ across the detector 28. The dc blocking capacitors C1 and C2 couple this light level responsive ac component to the differential input of the operational amplifier QA, the output of which is the difference of the voltages appearing at terminals 91 and 92. Since the voltage at terminal 92 is negative with respect to the voltage at terminal 91, the algebraic summation of these voltages doubles the input from the detector 28 while canceling out all unwanted signals unintentionally coupled into both signals. This high common mode rejection circuit cancels all noise and ripple currents introduced through interconnecting wiring, power supply noise and ripple, and reduces instability caused by component temperature drift.

After each sequence of output pulses from the detector 28 (FIG. 4) in response to a single revolution of the wheel 36, the decoder circuit 65 produces a switch control signal on the line 97. These signals are triggered by the periodic pulses 59′ (FIG. 6) from the commutator sensor 59. In response to the signals on the line 97, the control circuit 96 momentarily closes the switch 95. The resultant grounding of the amplified output of the photodetector 28 establishes a known base dc level desirable for accurate signal amplitude measurement. This dc restoration system prevents changes in dc output base levels that would result from varying levels in ambient light reflected from the sample 27 onto the photodetector 28.

Figure 9:
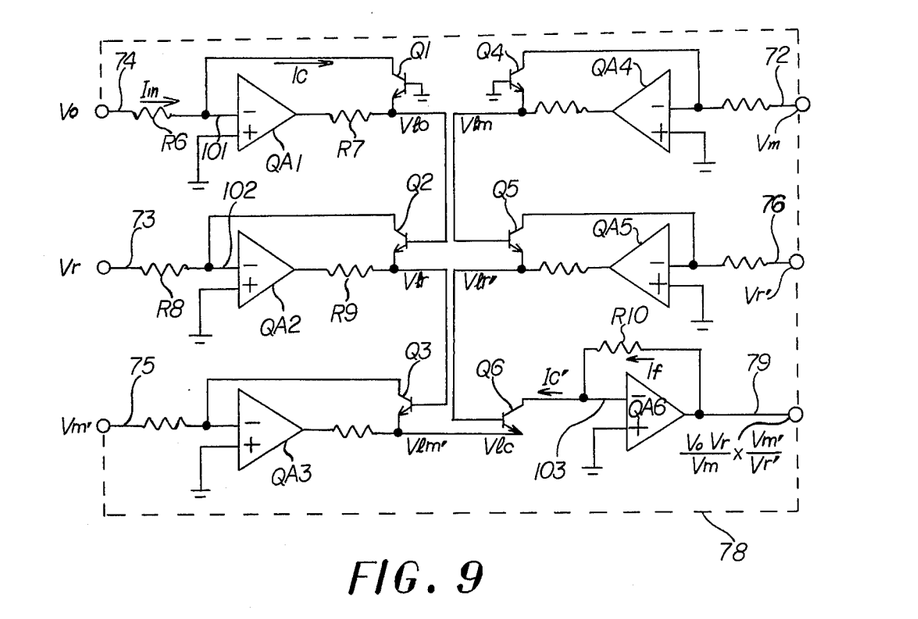
FIG. 9 is a schematic circuit diagram of a processor circuit shown in FIG. 7.

Referring now to FIG. 9 there are shown circuit details of the processor circuit 78 shown in FIG. 7. The voltage $V_o$ on the line 74 is applied through an input resistor R6 to an input 101 of an operational amplifier QA1, the other input of which is grounded. The amplifier input 101 is connected also to the collector of a transistor Q1, the base of which is grounded. Connecting the emitter of the transistor Q1 to the output of the amplifier QA1 is a resistor R7. Similarly, the signal voltage $V_r$ on the line 73 is applied through an input resistor R8 to an input 102 of an operational amplifier QA2, the other input of which is grounded. Also connected to the input 102 is the collector of a transistor Q2 the base of which is connected to the emitter of the transistor Q1. The emitter of the transistor Q2 is connected by a resistor R9 to the output of the amplifier QA2. In the same manner, the signal voltages $V_{m'}$ on the line 75, $V_m$ on the line 72 and $V_{r'}$ on the line 76 are applied, respectively, to circuits including an operational amplifier QA3 and a transistor Q3, an operational amplifier QA4 and a transistor Q4, and an operational amplifier QA5 and a transistor Q5. Finally, the emitter of the transistor Q3 and the emitter of the transistor Q5 are connected, respectively, to the emitter and base of a transistor Q6, the collector of which is connected to an input 103 of an operational amplifier QA6. The other input of the amplifier QA6 is grounded. Also connected to input 103 by a resistor R10 is the output of the amplifier QA6 which output appears on the signal line 79 shown in FIG. 7.

The base-emitter voltage $V_{lo}$ of the transistor Q1 is a voltage proportional to a log value of its collector current $I_c$. Since the inverting input of the amplifer QA1 must equal its non-inverting input, both of which are 0 volts, the collector current $I_c$ is equal to the input current $I_{in}$ and $I_{in}$ is equal to $V_o/R6$. Therefore $V_{lo}$ is proportional to the log of $V_o/R6$ and since R6 is constant $V_{lo}$ is proportional to the log of $V_o$. Similarly, the base-emitter voltage $V_{lr}$ of the transistor Q2 is proportional to the log of the input voltage $V_r$, the base-emitter voltage $V_{lm'}$ of the transistor Q3 is proportional to the input voltage $V_{m'}$, the base-emitter voltage $V_{lm}$ of the transistor Q4 is proportional to the input voltage $V_m$ and the base-emitter voltage $V_{lr'}$ of the transistor Q5 is proportional to the input voltage $V_{r'}$. Thus, the circuits receiving the input voltages $V_o$, $V_r$, $V_{m'}$, $V_m$ and $V_{r'}$ function as log converters. Conversely, the base-emitter voltage $V_{lc}$ of the transistor Q6 is proportional to the log of its collector current $I_{c'}$ or $I_{c'}$ is proportional to $10^{-(V_{lc})}$. Since $I_{c'}$ is equal to the current $I_f$ through the resistor R10, the output voltage on the line 79 is equal to $I_f \times R10$. That voltage, therefore, is proportional to $10^{-(V_{lc})}$ and the transistor Q6 functions as an antilog converter for the voltage $V_{lc}$. Following the circuit between the grounded bases of the transistors Q1 and Q2, it will be noted that the base-emitter voltage $V_{lc}$ of the transistor Q6 is a composite log signal equal to $V_{lo} + V_{lr} + V_{lm'} - V_{lr'} - V_{lm}$. Therefore, applying the characteristics of logarithms, the output voltage on line 79 is equal to $$\frac{V_o V_r}{V_m} \times \frac{V_{m'}}{V_{r'}}$$

which as noted above is a temperature compensated representation of sample moisture content.

Figure 10:
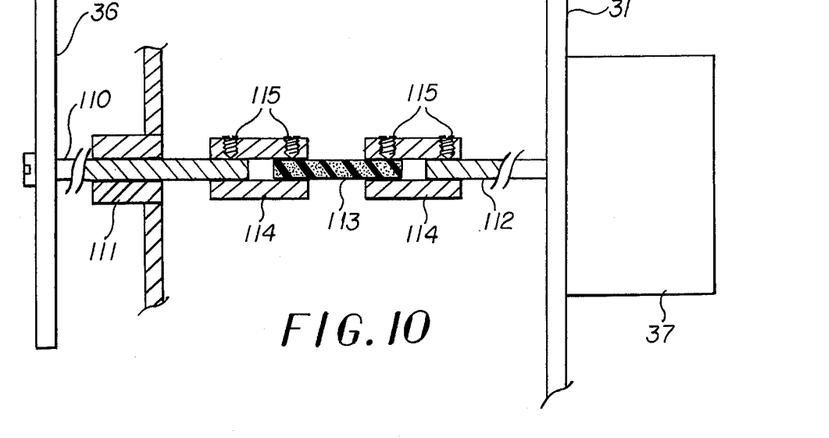
FIG. 10 is a schematic cross-section view of a drive motor-rotary wheel coupling assembly shown in FIG. 2.

FIG. 10 shows in greater detail the rotary wheel-motor coupling 38 diagrammatically illustrated in FIGS. 1 and 2. Secured to the rotary wheel 36 is a rigid wheel shaft 110 rotatably supported by a bearing 111. A motor shaft 112 is rotatably coupled to the motor 37 mounted on the support plate 31. Positioned between and axially aligned with the wheel shaft 110 and the motor shaft 112 is a flexible shaft 113. The flexible shaft 113, made for example of rubber, establishes a lost motion coupling between the wheel shaft 110 and the motor shaft 112. Connecting the flexible shaft 113 for rotation with the shafts 110 and 112 are a pair of collars 114 secured by a plurality of set screws 115.

The lost motion coupling 38 reduces the start-up torque required of the motor 37. Consequently, a low cost small-sized motor with a low starting torque but sufficient running torque can be used to drive the rotary wheel 36. Such motors have low heat dissipation which is important in high temperature environments wherein minimum heat dissipation is desirable.

Figure 11:
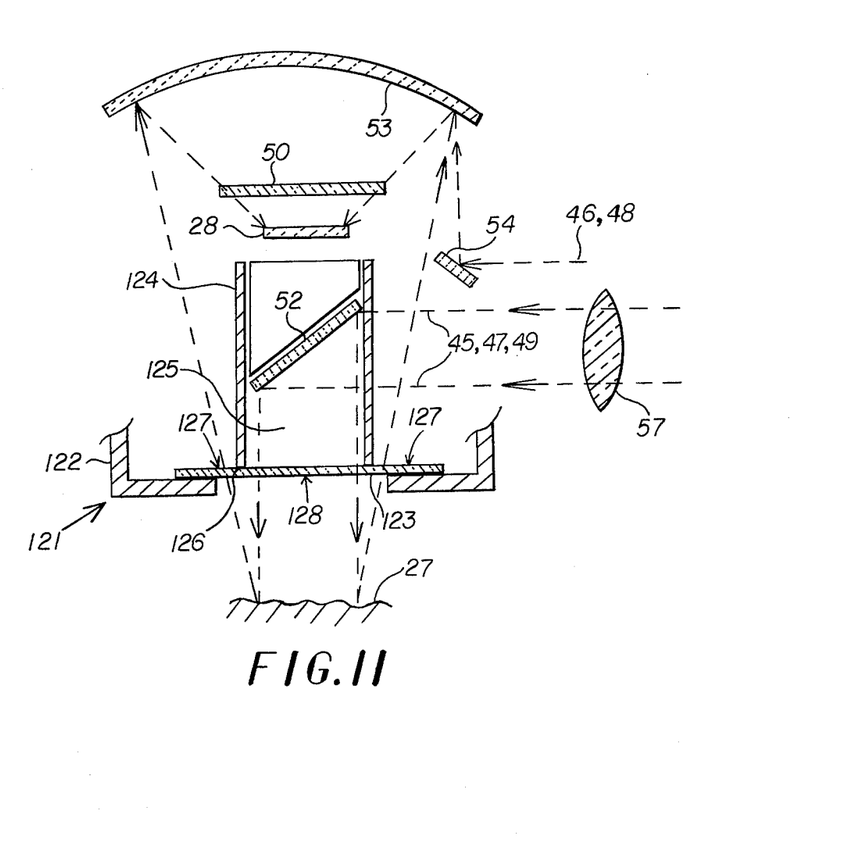
FIG. 11 is a schematic cross-sectional view of an optical director system shown in FIG. 1.

Partially illustrated in FIG. 11 is a housing 121 for the optical director system 26 and the photodetector 28 shown in FIG. 1. The housing 121 includes an optically dense casing 122 that substantially isolates the detector 28 from ambient light. Forming a bottom portion of the housing 121 is a flat light transmissive window 123 that transmits the beams 45, 47 and 49 to the sample 27 and reflected light therefrom to the domed mirror 53. An optically dense shield tube 124 is positioned within the housing 121 and encloses the beams 45, 47 and 49 during their passage between the reflective mirror 52 and the flat window 123. The shield tube 124 defines a volume 125 that is optically shielded from the photodetector 28 and has a light transmissive opening 126 located directly adjacent to an area 128 on the flat window 123. Thus, any light reflected by the window 123 incident to the passage of the beams 45, 47 and 49 to the sample 27 is returned to the volume 125 and prevented from reaching the photodetector 28. Conversely, light reflected from the sample 27 passes through an annular window portion 127 surrounding the window area 128 and is reflected by the domed mirror 53 onto the photodetector 28. Shielding the detector 28 from all light except that reflected from the sample 27 enhances the accuracy of the analyzer system. Furthermore, this desirable result is accomplished without the use of a relatively expensive domed window of the type normally used to prevent unwanted reflection.

Figure 12:
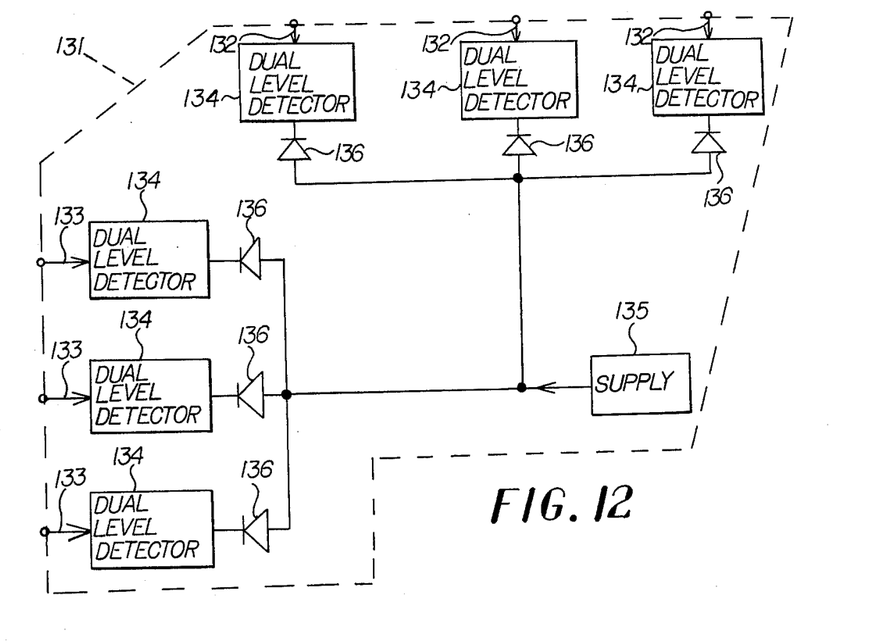
FIG. 12 is a schematic block diagram of a fault detector circuit shown in FIG. 7.

Referring again to FIG. 7, there is shown a fault detector circuit 131 that receives a plurality of signals on lines 132 from the processor circuit 78 and a plurality of signals on lines 133 from the decoder circuit 65. The signals on each of the lines 132 and 133 is either a key operating voltage in a distinct printed circuit board (not shown) or an average dc signal voltage indicative of the presence or absence of signal pulses in such a board. As shown in FIG. 12, each of the signal voltages on the lines 132 and 133 is applied to a dual level detector circuit 134 in the detector circuit 131. Connected between each of the level detector circuits 134 and a supply 135 is a light emitting diode 136. If the incoming signal level on any line 132, 133 is above or below a predetermined limit, the level detector circuit 134 receiving that signal energizes its associated light emitting diode 136. The visible signal thus established indicates the specific circuit board in which a fault condition has occurred. Consequently, location and elimination of the fault condition is simplified.

Obviously, many modifications and variations of the present invention are possible in light of the above teachings. It is to be understood, therefore, that the invention can be practiced otherwise than as specifically described.

What is claimed is:

1. Analyzer apparatus comprising:
   radiant energy source means;

first optical means for receiving radiant energy from said source means and producing first and second radiant energy beams having the same given band of wavelength;

second optical means for receiving radiant energy from said source means and producing third and fourth radiant energy beams having a common band of wavelength different than said given band;

photodetector means;

radiant energy director means for directing said first and third beams first to a sample being analyzed and then to said photodetector means and directing said second and fourth beams to said photodetector means; and output means for comparing the energy levels of said beams as detected by said photodetector means.

2. Apparatus according to claim 1 wherein said photodetector means produces a signal $V_m$ dependent upon the energy level of said first beam, a signal $V_r$ dependent upon the energy level of said third beam, a signal $V_{m'}$ dependent upon the energy level of said second beam, and a signal $V_{r'}$ dependent upon the energy level of said fourth beam, and said output means comprises signal processor means for producing an output signal dependent upon the relationship $$\frac{V_r}{V_m} \times \frac{V_{m'}}{V_{r'}}.$$

3. Apparatus according to claim 2 wherein said first optical means comprises a first optical filter, and said second optical means comprises a second optical filter.

4. Apparatus according to claim 3 wherein said first and second optical means comprise collimator means for receiving energy from said source means and producing therewith a measure radiant energy beam and a compensating radiant energy beam, and motive means for moving said first optical filter alternately into said measure beam to produce said first beam and into said compensating beam to produce said second beam, and moving said second optical filter alternately into said measure beam to produce said third beam and into said compensating beam to produce said fourth beam.

5. Apparatus according to claim 4 wherein said motive means comprises a rotary wheel supporting said first and second optical filters.

6. Apparatus according to claim 5 wherein said collimator means comprises accumulator means for providing a higher radiant energy level in said measure beam than in said compensating beam.

7. Apparatus according to claim 5 including adjustable energy attenuation means for adjusting the radiant energy levels of said second and fourth beams.

8. Apparatus according to claim 5 wherein said first and second filters are mounted on said rotary wheel in positions equally spaced from its center of rotation, and said measure and compensating beams are sized and oriented to pass through equally sized portions of said first and second filters.

9. Apparatus according to claim 8 wherein said measure and compensating beams are focused upon substantially diametrically opposed locations on said rotary wheel.

10. Apparatus according to claim 9 wherein said first and second filters are mounted on said rotary wheel in positions angularly spaced apart by between 50°–130°.

11. Apparatus according to claim 5 wherein said photodetector means comprises a photodetector that sequentially receives said first, second, third and fourth beams and produces an ac signal with values determined by the energy levels thereof; and including decoder means for identifying the portions of said ac signal determined by each of said first, second, third and fourth beams.

12. Apparatus according to claim 11 including commutator means for producing timing pulses received by said decoder means and indicating periods of coincidence between said first and second filters and said measure and compensating beams.

13. Apparatus according to claim 12 wherein said commutator means comprise a commutator radiant energy source associated with each of said first and second filters and movable with said rotary wheel, and commutator energy detector means energized by said commutator sources in certain angular positions thereof.

14. Apparatus according to claim 12 wherein said commutator means comprises initiator means for producing periodic pulses received by said decoder means and identifying the sequence of said timing pulses.

15. Apparatus according to claim 14 wherein said commutator means comprise a commutator radiant energy source associated with each of said first and second filters and movable with said rotary wheel, and commutator energy detector means energized by said commutator sources in certain angular positions thereof.

16. Apparatus according to claim 15 wherein said initiator means comprises initiator radiant energy source means movable with said rotary wheel and energizing said commutator detector means distinguishably from said energization thereof by said commutator sources.

17. Apparatus according to claim 16 including reset means activated by said periodic pulses by said initiator means to periodically ground the output of said photodetector.

18. Apparatus according to claim 2 including reset means for periodically grounding the output of said photodetector means so as to establish a base dc level for measurement of said signals.

19. Apparatus according to claim 2 wherein said signal processor means comprises log converter means for producing log signals proportional to log values of said signals, $V_r$, $V_{r'}$, $V_m$ and $V_{m'}$; summing means for producing a composite log signal having a value proportional to the sum of said log values of said signals $V_r$ and $V_{m'}$ less the sum of said log values of said signals $V_{r'}$ and $V_m$; and antilog converter means for producing an analog output signal having a value proportional to an antilog value of said composite signal.

20. Apparatus according to claim 19 wherein said log converter means comprise first, second, third and fourth transistors; circuit means for producing collector currents proportional to $V_r$ in said first transistor, to $V_m$ in said second transistor, to $V_{r'}$ in said third transistor, and to $V_{m'}$ in said fourth transistor; circuit means for combining the base-emitter voltages of said transistors to produce said composite signal; an antilog transistor; and circuit means producing for said antilog transistor a base-emitter voltage proportional to the value of said composite signal and a collector current having a value proportional to the value of said analog output signal.

21. Apparatus according to claim 20 wherein said first optical means comprises a first optical filter, and said second optical means comprises a second optical filter.

22. Apparatus according to claim 21 wherein said first and second optical means comprise collimator means for receiving energy from said source means and producing therewith a measure radiant energy beam and a compensating radiant energy beam, and motive means for moving said first optical filter alternately into said measure beam to produce said first beam and into said compensating beam to produce said second beam, and moving said second optical filter alternately into said measure beam to produce said third beam and into said compensating beam to produce said fourth beam.

23. Apparatus according to claim 22 wherein said motive means comprises a rotary wheel supporting said first and second optical filters.

24. Apparatus according to claim 23 wherein said photodetector means comprises a photodetector that sequentially receives said first, second, third and fourth beams and produces an ac signal with values determined by the energy levels thereof; and including a decoder means for identifying the portions of said ac signal determined by each of said first, second, third and fourth beams.

25. Apparatus according to claim 24 including commutator means for producing timing pulses received by said decoder means and indicating periods of coincidence between said first and second filters and said measure and compensating beams.

26. Apparatus according to claim 2 wherein said photodetector means is positioned so as to receive said first and third beams after reflection thereof from the sample.

27. Apparatus according to claim 13 wherein said commutator sources comprise reflective surfaces on said rotary wheel and a light source for directing light toward said reflective surfaces.

28. Apparatus according to claim 2 wherein said first and second beams have a narrow bandwidth centered at approximately 1.9 microns and said third and fourth beams have a narrow bandwidth centered at approximately 1.8 microns.

29. Analyzer apparatus comprising:
radiant energy source means;
first optical means for receiving radiant energy from said source means and producing a measure beam of radiant energy;
second optical means for receiving radiant energy from said source means and producing a reference beam of radiant energy;
a photodetector having a variable resistance dependent upon the level of radiant energy received;
radiant energy director means for directing said measure and reference beams first to a sample being analyzed and then to said photodetector;
power supply means establishing a voltage across said photodetector;
a balanced differential input circuit receiving said voltage across said photodetector; and
output means for receiving the variable output of said differential input circuit and producing an output signal representing the difference in energy levels between said measure and reference beams.

30. Apparatus according to claim 29 wherein said balanced differential input circuit comprises an operational amplifier having inputs connected to output terminals of said photodetector and said power supply comprises equal and opposite voltage supplies, one connected to each of said output terminals.

31. Apparatus according to claim 30 wherein said input circuit further comprises a load resistor connected between each of said voltage supplies and one of said output terminals and a pair of coupling capacitors one connected between each of said inputs of said operational amplifier and one of said output terminals of said photodetector.

32. Analyzer apparatus comprising:
radiant energy source means;
first optical means for receiving radiant energy from said source means and producing a measure beam of radiant energy;
second optical means for receiving radiant energy from said source means and producing a reference beam of radiant energy;
photodetector means;
radiant energy director means for directing said measure and reference beams first to a sample being analyzed and resultant reflected energy to said photodetector means;
a housing retaining said energy director means and said photodetector means, said housing comprising a flat window for first transmitting said beam to the sample and then transmitting said reflected energy to said photodetector means and optical shield means for shielding said photodetector means from radiant energy reflected by said window incident to said transmission of said beams to the sample;
output means for comparing the energy levels of said beams as detected by said photodetector means.

33. Apparatus according to claim 32 wherein said optical shield means comprises an optically dense tube retained by said housing and enclosing said beams, said tube defining a volume optically shielded from said photodetector means and an opening for transmitting said beams to the sample, and wherein said opening is directly adjacent to a given area of said window such that all radiant energy reflected by said window incident to transmission of said beams is received by said volume.

34. Apparatus according to claim 33 wherein said window includes an annular portion around said given area, and said reflected energy from the sample is transmitted by said annular portion.

35. Analyzer apparatus comprising:
radiant energy source means;
first optical means for receiving radiant energy from said source means and producing a measure beam of radiant energy;
second optical means for receiving radiant energy from said source means and producing a reference beam of radiant energy;
photodetector means;
radiant energy director means for directing said measure and reference beams first to a sample being analyzed and then to said photodetector means;
processing circuit means responsive to said photodetector means and producing an output signal indicative of the relative energy levels of said measure and reference beams received by said photodetector means; and
fault detector means for monitoring voltage levels in said processing circuit means and producing a fault indication in response to the occurrence of voltage levels above or below a given range.

36. Apparatus according to claim 35 wherein said detector means comprises a plurality of fault detectors each monitoring a different voltage in said processing circuit means and producing a distinguishable fault indication in response to fluctuations of said different voltages beyond predetermined ranges.

37. Apparatus according to claim 36 wherein each of said plurality of fault detectors comprises a dual level detector circuit for receiving said different voltage, and a signal light energized in response to detection of said fluctuations by said dual level detector circuit.

38. A method for analyzing the composition of a sample and including the steps of:
  producing first and second radiant energy beams having the same given band of wavelength;
  producing third and fourth radiant energy beams having a common band of wavelength different than said given band;
  directing said first and third beams to the sample being analyzed;
  determining the resultant energy level ratio of said first and third beams; and
  compensating said resultant energy level ratio with a comparison energy level ratio of said second and fourth beams.

39. A method according to claim 38 wherein said producing steps comprise the steps of:
  producing a measure radiant energy beam;
  producing a compensating radiant energy beam;
  sequentially passing said measure beam through a first optical filter to produce said first beam and through a second optical filter to produce said third beam;
  sequentially passing said compensating beam through said first filter to produce said second beam and through said second optical filter to produce said fourth beam.

40. A method according to claim 39 wherein said compensating step comprises reducing the energy level of said first beam by an amount proportional to the energy level of said second beam and reducing the energy level of said third beam by an amount proportional to the energy level of said fourth beam.

* * * * *